United States Patent [19]

Mitra

[11] Patent Number: 5,435,169
[45] Date of Patent: Jul. 25, 1995

[54] CONTINUOUS MONITORING OF ORGANIC POLLUTANTS

[75] Inventor: Somenath Mitra, Edison, N.J.

[73] Assignee: New Jersey Institute of Technology, Newark, N.J.

[21] Appl. No.: 76,414

[22] Filed: Jun. 14, 1993

[51] Int. Cl.⁶ ............................................. G01N 30/14
[52] U.S. Cl. ................................................... 73/23.41
[58] Field of Search ................... 73/23.35, 23.41, 23.42

[56] References Cited

U.S. PATENT DOCUMENTS

| | | | |
|---|---|---|---|
| 3,451,255 | 6/1969 | Neville et al. | 73/23.41 X |
| 3,483,731 | 12/1969 | Sanford et al. | 73/23.35 |
| 3,675,466 | 7/1972 | Linenberg | 73/23.42 X |
| 4,399,688 | 8/1983 | Dennis | 73/23.35 |
| 5,014,541 | 5/1991 | Sides et al. | 73/23.41 |
| 5,123,276 | 6/1992 | Hartman et al. | 73/23.41 |
| 5,261,937 | 11/1993 | Jiang et al. | 73/23.41 X |

FOREIGN PATENT DOCUMENTS

| | | | |
|---|---|---|---|
| 142357 | 6/1991 | Japan | 73/23.41 |
| 170838 | 7/1991 | Japan | 73/23.41 |
| 1341575 | 9/1987 | U.S.S.R. | 73/23.41 |

Primary Examiner—Hezron E. Williams
Assistant Examiner—Joseph W. Roskos
Attorney, Agent, or Firm—Klauber & Jackson

[57] ABSTRACT

A method and device for the continuous monitoring of very low level concentrations of materials such as volatile organic compound (VOC) pollutant levels in a fluid (gaseous or liquid) stream, including stack gases and waste water. The fluid stream passes through an on-line micro sorbent trap (OLMT) for entrapment of VOCs. The pollutants are concentrated in the OLMT and electrically rapidly heated to simulate an injection into a gas chromatograph system or other detector. The concentration and heating steps are effected at predetermined time intervals and temperature conditions with correlation to known fluid flow rates. Pollutants separate in the chromatographic column with a chromatograph being obtained with each injection for identification of pollutants and respective pollution levels. Alternatively, without chromatograph, a single peak is obtained which represents the total quantity of pollutants in the fluid stream. The OLMT enhances sensitivity such that low concentrations can be accurately measured on a continuous basis. The device can further include a sampling valve which samples the fluid stream into the OLMT and then connects the OLMT with a GC carrier gas to avoid incompatible gas flow through the OLMT or the GC detector.

37 Claims, 11 Drawing Sheets

CONTINUOUS MONITORING OF ORGANIC POLLUTANTS

FIELD OF THE INVENTION

This invention relates to methods and devices for continuous monitoring of compounds of interest, such as pollutants in fluid streams and particularly to the continuous monitoring of low level concentration volatile organic compound (VOCs), in fluid streams such as stacks, effluents from air toxic control devices, waste water and drinking water.

BACKGROUND OF THE INVENTION

There is presently no known efficient and accurate device or method for the continuous, real-time monitoring of volatile organic compounds in fluid streams, even though such pollutants have received much attention recently and many VOCs are toxic or carcinogenic even in trace amounts and lead to ozone formation in the troposphere. Examples of common volatile organic pollutants include aliphatic and aromatic hydrocarbons such as hexane and benzene; chlorinated organics such as vinyl chloride, dichloro ethane; oxygenated compounds such as methanol, methylethylketone and also nitrogen or sulfur containing compounds. However, the VOCs are usually present in low concentrations (sub $ppm_v$ and even sub $ppb_v$ levels) and it is difficult to accurately monitor them on a continuous basis.

Without the means for continuous monitoring, it is the current practice to utilize whole air samplers such as tedlar bags and canisters (e.g. EPA method TO14) or sorbent cartridges. With whole air samplers, several liters of a sample are collected and taken to a laboratory for analysis.

With the sorbent based methods, the sample is passed through a cartridge containing one or more adsorbents such as Tenax, XAD-2 and charcoal where the VOCs are trapped (EPA Method T01, EPA Method 5). Thereafter, the analytes are thermally desorbed or solvent extracted for analysis. Measurement of low concentrations is achieved by concentrating the analyte from a large volume of sample, with such measurements being made at off-site laboratory facilities.

While such methods are generally effective and accurate, the samples are normally transported to the laboratory for analysis by gas chromatography (GC) with a suitable detector. Accordingly, they cannot be utilized for continuous on-line analysis to provide information on a real-time basis as required for effective pollution control and for meeting regulatory requirements.

An important feature of any continuous, on line GC analysis is the means by which the sample is introduced to the analytical column. The injection band should be sharp (usually less than a second wide) to provide good GC resolution. Multi-port sample valves are used as injectors in continuous GC monitoring analysis. The valves use a sample loop for injection with typical injection volumes ranging from a few microliters to 1-2 milliliters for capillary columns. These valves automatically make injections from a sample stream, on an intermittent basis, to the GC column. However these valves have definite limitations, foremost of which is that the injected sample size is only between a few microliters to at most a few milliliters. Small samples produce a small signal and lower the sensitivity and increase detection limits. Detection becomes a problem particularly with sample streams that have sub parts per million or per billion concentration levels. Although desirable, the injection of larger sample quantities from large loops causes excessive band broadening and degradation of chromatographic resolution. Sample valves are therefore inadequate for accurate environmental monitoring of VOC concentrations.

SUMMARY OF THE INVENTION

Generally the present invention comprises a device and method for the continuous, near real-time, monitoring of very low level concentration (sub $ppm_v$ and even sub $ppb_v$) of volatile organic compound (VOC) pollutants in a fluid stream for environmental monitoring and control purposes. The device has general utility in effectively continuously monitoring any low level concentrations of materials in fluid streams.

More specifically, the present invention comprises a method for the continuous monitoring of concentrations, on the order of at most $ppm_v$, of volatile organic compound (VOC) pollutant levels in a fluid stream. The method comprises the steps of collecting at least one sample of the VOCs, by collecting means, from the fluid stream and concentrating collected samples of the VOCs by concentration means. At predetermined time periods, the concentrated, collected samples of the VOCs are desorbed from the concentration means, by desorption means, and the desorbed, concentrated, collected samples of the VOCs are injected into a detector. The steps are repeated for continuous monitoring. Detectors specifically include GC detectors (e.g., FID, NPD, FPD, TID, TCD, ECD), mass spectrometer, FTIR non-methane organic carbon analyzers, as well as sensors in general.

A device, in accordance with the present invention, which is capable of the continuous monitoring of concentrations, on the order of less than $ppm_v$, of materials in a fluid stream, comprises a multiport sampling valve, a concentrator element and a concentration detector. The valve comprises a sample retention element, with the valve periodically switching to cause a sample of the stream, with contained materials, to enter and be retained in the sample retention element. The valve is further connected to a source of an inert carrier gas, wherein the sample is entrained on the carrier gas and carried to the concentrator element from the sample retention element. The concentrator element has means for collecting and retaining substantially only the materials being monitored. The concentrator element further has injection means to inject at least one sample of the materials into the detector to effect the monitoring.

More specifically, a device in accordance with the present invention combines a sampling valve with a small diameter tube packed with an adsorbent, referred to hereinafter as an on-line microtrap (OLMT). The OLMT may also be made from a piece of a capillary column. As described above, though a valve may be used to inject samples from a stream onto a GC column, only a small sample can be used to avoid band broadening. With the device of the present invention, large sample volumes may be injected from a valve, with a large sample loop, into the OLMT, where the analytes of interest are trapped until a sufficiently large sample accumulates. The OLMT is thereafter heated to generate a sharp concentrated analyte injection (or pulse) for the GC analysis. The valve and the OLMT injections are synchronized and can be made at fixed intervals of time (every few seconds to hours). Corresponding to each injection from this device, a chromatogram is obtained. Alternatively, several injections may be made from a valve having a small sample loop followed by an injection pulse from the OLMT. In either embodiment, the sample is accumulated by the OLMT, which is then pulsed to generate an injection. The device may be used for continuous monitoring by making a series of injections or can be used for making discrete concentrated single injections.

The OLMT pre-concentrates analytes from a large injection volume. The OLMT is provided with automated thermal desorption means so that it can be heated in very short period of time (from a few milliseconds to a few seconds). The desorption of the analytes is rapid enough that this pulse will serve as the injection for the GC column. The OLMT therefore, serves the dual purpose of sample concentration and injection. The different components in the sample thereafter separated by the GC column and analyzed by a detector. The measurement may also be done without a GC column. If a GC column is not used, a measure of the sum total of the different components is measured by the detector.

In accordance with the present invention, an OLMT can also surprisingly be effectively used, without the valve, in continuous very low concentration level detection such as of VOCs, as described. The VOCs from a fluid stream are passed directly through the OLMT, wherein they are trapped, collected and concentrated for a specific time period and then the OLMT is rapidly pulsed to generate an injection for the GC analysis. The OLMT can be pulsed at fixed intervals of time to generate a series of chromatograms. It is possible in all instances, if appropriately regulated such as with a synchronized heating sequence, to use several OLMTs in series, particularly with each being designed to concentrate different materials. The OLMT may be used in other configurations with one or more valves, but in effect, will serve the dual purpose of sample concentration and injection into the GC system.

With either of the embodiments, the monitoring device is not removed from the monitored site and the desorption/analysis is done on-site. As a result, monitoring is continuous, with the pre-concentration increasing the sensitivity.

In liquid streams, a membrane separation or purging by an inert gas such as $N_2$ is used to separate the organics from a fluid carrier such as an aqueous matrix. The membrane separation is also applicable to gaseous streams such as air. In such embodiment, the VOCs that permeate through the membrane are carried by a stream of inert gas (He, $N_2$ etc.) to the OLMT or the valve/OLMT injection device for GC analysis. In the case of purging, the purged pollutants are concentrated and injected by the OLMT.

It is an object of the present invention to provide accurate on-line, substantially continuous, monitoring of very low concentration VOC levels in fluid streams and a device for effecting such monitoring.

It is a further object of the present invention to provide such continuous monitoring of VOC levels by utilizing a sample pre-concentrator which effectively builds up concentration levels for normal GC monitoring.

It is a still further object of the present invention to provide the pre-concentrator with automated thermal desorption, so that it serves the dual purpose of sample concentration and injection at short term periodic intervals.

It is yet another object of the present invention to provide such monitoring of VOC levels in both gas and liquid streams.

These and other objects, features and advantages of the present invention will become more evident from the following discussion and drawings in which:

DETAILED DESCRIPTION OF THE INVENTION

Figure 1:
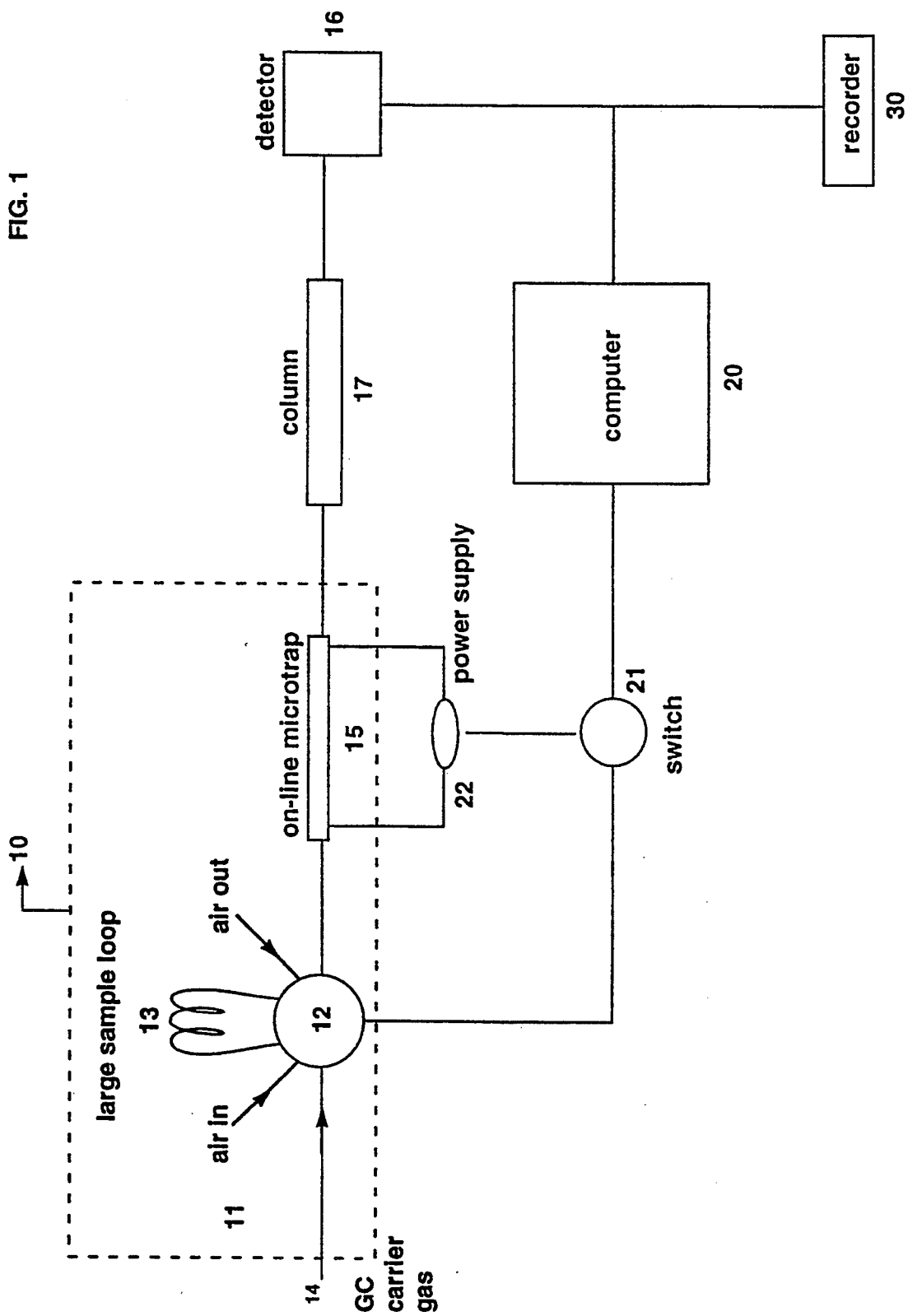
FIG. 1 is a schematic diagram of a combination valve and OLMT device of the present invention.

The sampling valves utilized in the device of the present invention are multi-port valves commonly used as GC injectors. In such usage, the valves withdraw a small quantity of the sample from a stream and inject it directly to the GC column. They are accordingly used for large concentration measurements and are ineffective for use in low concentration samples (sub ppm$_v$ and ppb$_v$ levels) since only a small injection volume can be used for reasonable chromatographic separation and analysis with insufficient sample material available to provide accurate measurements. In accordance with the present invention the valve does not make a direct injection to the column. Instead, the valve injects a large volume to the OLMT which selectively traps the materials of interest. Heating of the OLMT generates a desorption pulse, which serves as the injection to the GC column. The desorption pulse is sharp enough to serve as an injection for the GC column, no matter how large a sample is injected from the sample loop. Since this device allows effective use of large injection volumes, lower concentrations are accurately measured and higher sensitivity is obtained. Multi-port valves can also be plumbed to permit the device to be used in monitoring more than one sample stream.

Large sample quantity injections may be made in several alternative procedures. A large sample loop may be used to make one large injection without detrimental GC band broadening. Alternately, instead of one large sample volume, a series of small injection volumes may be injected from the valve to the OLMT prior to GC injection. In either case, the components are trapped by the OLMT and then injected into the GC column.

In accordance with a preferred embodiment of the present invention, the OLMT is made of a small length of metallic (such as of stainless steel, or silica lined stainless steel) or of fused silica tubing. The tubing is packed with an adsorbent or a liquid chromatographic stationary phase. The adsorbent may be a carbon based or polymeric material. Some examples of suitable adsorbents include commercially available Carbotrap, Carboxen, Carbosieves, Tenax, Chromosorbs, etc. The amount of adsorbent contained in the trap should be sufficient to provide enough accessible adsorption sites so that the sample does not break through from the OLMT to the GC column, before an injection is made. For many environmental applications it may be necessary that the adsorbent material should be selectively able to reject water vapor, other gases, and should not react with oxygen because these are commonly found in environmental samples and would detrimentally limit available adsorption sites.

It is important that the OLMT does not have too much thermal mass in order that there be rapid heat diffusion therein, on the order of no more than several seconds, to generate the requisite sharp desorption or injection band. Typical internal diameters of the OLMT may vary from 0.05 to 2 mm depending upon the type of GC column being used and its injection speed requirements. For example, for megabore capillary columns, an OLMT with a 0.5 mm i.d. has been found to operate satisfactorily. The packing length within the OLMT tube effectively ranges from 2 mm to 25 cm.

In effecting the thermal desorption, an OLMT comprised of a metallic tube is preferably heated by passing the current directly through the metal wall. External heating tape or other heating element such as a microwave or hot air heater may also be used. In order to effect the thermal desorption of an OLMT comprised of fused silica tubing, the fused silica tubing should be coated with an electrical paint or suitable heating element.

For continuous operation, the valve and the heat pulse to the OLMT are controlled by a programmable controller such as by a controlling computer with appropriate software and hardware. The valve injection and the heat pulse should be synchronized in order to provide sufficient time for the sample to migrate from the valve to the OLMT. However, the time difference between both events should not be too large whereby the sample breaks through the OLMT.

Continuous monitoring may also be done by using only an OLMT without a valve, with the effluents being continuously carried into the OLMT. Such effluents or fluids may either be the actual flow of stack gas or, as may be necessary in many instances, the effluent is diluted with a carrier gas such as $N_2$ or He. In accordance with the present invention, with the operation of continuous monitoring, the injections or pulses are made at fixed intervals of time and, corresponding to each pulse, a chromatogram is obtained. The OLMT may be plumbed or configured in a different geometry, such as with one or more valves, but will always serve the dual purpose of sample concentration and injection. Since the amount of VOC trapped is proportional to the concentration of the stream (taken at predetermined set intervals) passing through it, the response is proportional to sample concentration and pollutant levels.

Though modulators of a similar type have been utilized in laboratory chromatographic analysis, in most of these applications, the temperature of a small segment of a capillary column is thermally modulated to generate a modulation signal from the sample being carried by the mobile phase. These modulations have been done at the head of a column, as well as, in the middle of two columns in multi-dimensional chromatography. In contrast, the OLMT operation of the present invention differs, as being akin to a small sorbent trap, put on-line with the sample stream and operated at fixed intervals of time. The microtrap traps the sample for a period of time before releasing it as a desorption pulse.

Modulators have been used in laboratory settings for analytical sample measurements as a means for introducing samples (e.g. $H_2S$ for testing) from a carrier gas. They have never been used for monitoring very low level VOCs from fluid streams in an environmental testing setting. Their efficacy for such purpose has never been demonstrated, particularly with the low concentration levels of VOCs in stack or stream environments. In addition, modulators comprise low level absorbers (a requirement necessary to produce a test-modulation signal) incapable of retaining volatile materials such as VOCs for the lengthy periods of time thought necessary for providing sufficient sample for effective measurement sensitivity. In order to effectively utilize the modulators for environmental control monitoring of very low level concentration VOCs, in accordance with the present invention, various condition factors must be adhered to, as will be described in the following discussion.

The adsorption and desorption processes play a key role in the operation of the OLMT for environmental monitoring of low VOC levels. The time for which the sample is retained in the OLMT is given by, $t_b$, with k being the capacity factor of the sample in the trap:

$$t_b = (k+1)L/u$$

where L is the length of OLMT, and u is the flow rate. In order to obtain a large signal at the detector, the OLMT must trap as much analyte as possible, before making an injection. To this end, trapping efficiency is defined as the fraction of the incoming sample retained by the trap before an injection is made. The injections are made at fixed intervals of time, and trapping efficiency, T:

$$T = \frac{t_b m_s}{t_i m_i}$$

$$T = \frac{t_b m_s}{t_i (m_s + m_m)}$$

where $m_s$ is the mass of the sample in the stationary phase; $m_i$ is the mass of the sample flowing into the OLMT; $m_m$ is the mass of the sample in the mobile phase; $t_i$ is the pulse interval. The equation reduces to $$T = (t_b/t_i)k/(k+1)$$

If the pulses are made very frequently such that $t_i < t_b$ then the micro sorbent trap accumulates samples only for $t_i$ and the equation becomes:

$$m = k/(k+1).$$

When pulse interval is less than $t_b$, the trapping efficiency is constant and is at its highest value and when the interval is increased higher than $t_b$, the trapping efficiency begins to decrease.

For a given VOC and OLMT, the temperature determines the capacity factor and in turn $t_b$. Trapping efficiency decreases with increases in temperature with a decrease paralleling the decrease in $t_b$, and with an approximate linear relationship therebetween. The above factors make temperature an important variable in OLMT operation. For example, the maximum attainable OLMT response at −10° C. can be more than six times than that at 35° C. Extremely low temperatures are however to be avoided since some VOCs may be irreversibly adsorbed at such low temperatures. In practice, the trap temperature is optimized for the analytes of interest and in many instances sub-ambient cooling may not be necessary, although it will tend to increase sensitivity and lower the detection limit.

In some applications, it is further preferred that the fluid stream, which may include both gaseous and liquid streams such as water, be initially fed through a hollow fiber membrane, purged with an inert gas which selectively removes the VOCs from the stream. Thereafter the VOCs are transported via a substantially inert carrier gas such as helium or nitrogen. The carrier gas is directed into the GC system for analysis. The injections from the gas stream will be made either using the OLMT or using the Valve/OLMT combination described above.

In order to more clearly illustrate the efficacy of the present invention, the following example of operation, testing, and parameter effects is presented. It is understood that such example is illustrative in nature and that details contained therein are not to be construed as limitations on the present invention.

EXAMPLE

The device 10 shown in FIG. 1, is operable with a gas stream 11 which passes through valve 12 having, for example, a large sample loop 13, such as with a volume of 13 ml, for retention of gas samples with contaminants, i.e., analyte. A switching of the valve 12, periodically, at preset intervals, causes sampling of the gas stream 11 and then connection of the GC carrier gas source 14 with OLMT 15 whereby the sampled analyte is directed into the OLMT for subsequent injection. Computer 20, with switch 21 and power supply 22, provided the requisite pulse timing and thermal desorption. Concentration level data from detector 16 was recorded on recorder 30. The trap was heated by turning on a current for a pre-specified duration and at fixed intervals of time between 5 to 300 seconds. The current duration was between 100 to 1000 msec.

Figure 2:
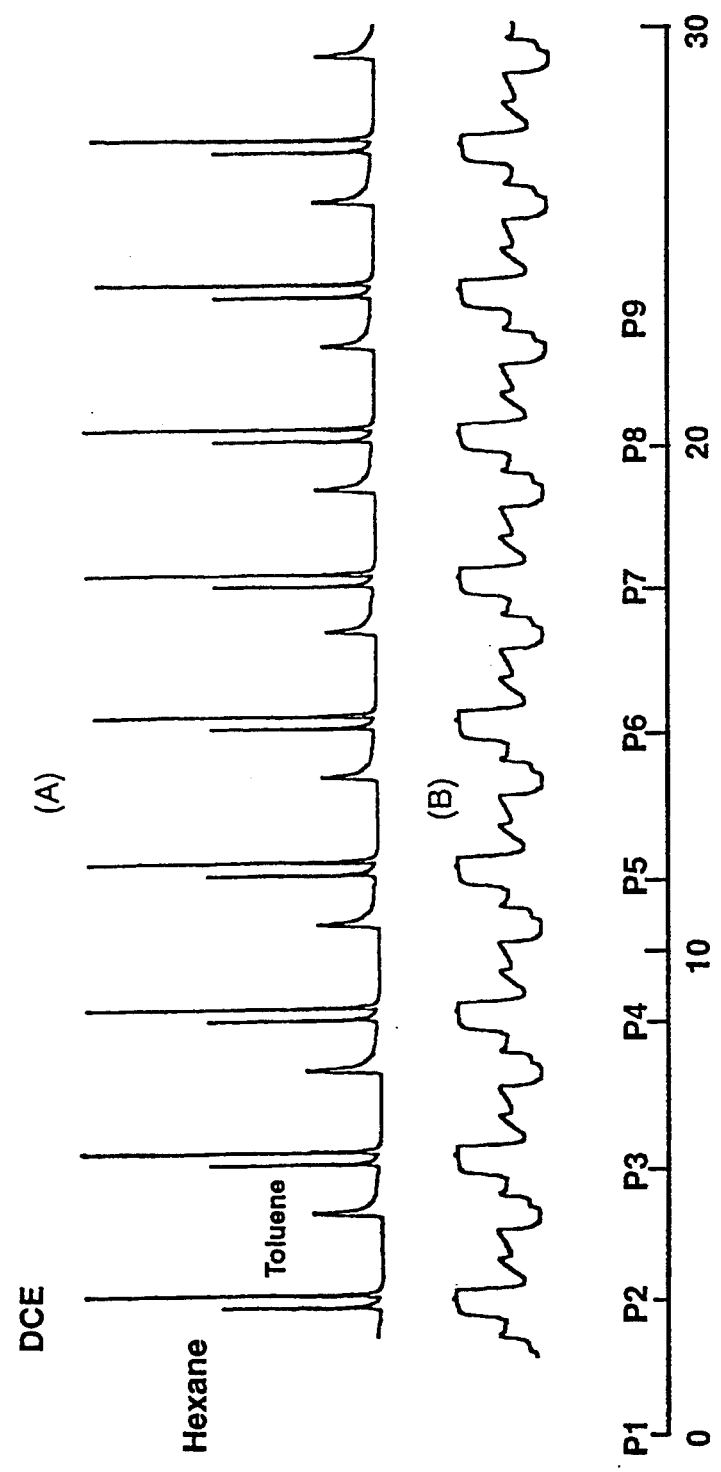
FIGS. 2A and 2B depict continuous monitoring of a stream containing low levels of VOCs. These figures provide a comparison of GC results of identical gas samples taken with single large loop valve injection, and the device of FIG. 1, respectively.

FIG. 2A is a series of chromatograms where a injections were made from the valve 12 of FIG. 1 into the GC column 17. The gas contained sub ppm$_v$ levels of toluene, hexane and dichloroethane (DCE). A 13 ml sample loop was used, which required two minutes to sweep the whole sample from the sample loop 13 to the GC column 17. The injection band is of a length reflecting such time. The resolution is poor and the peaks in FIG. 2B cannot be distinguished from one another.

In contrast, when the same sample from the 13 ml sample loop passed through the OLMT 15 prior to injection into GC column 17, it provided the chromatogram of FIG. 2A which clearly defined and separated peaks, readily amenable to accurate monitoring. The OLMT, even with a single large sample, eliminates the broad band chromatogram results present with the use of valves alone.

Figure 3:
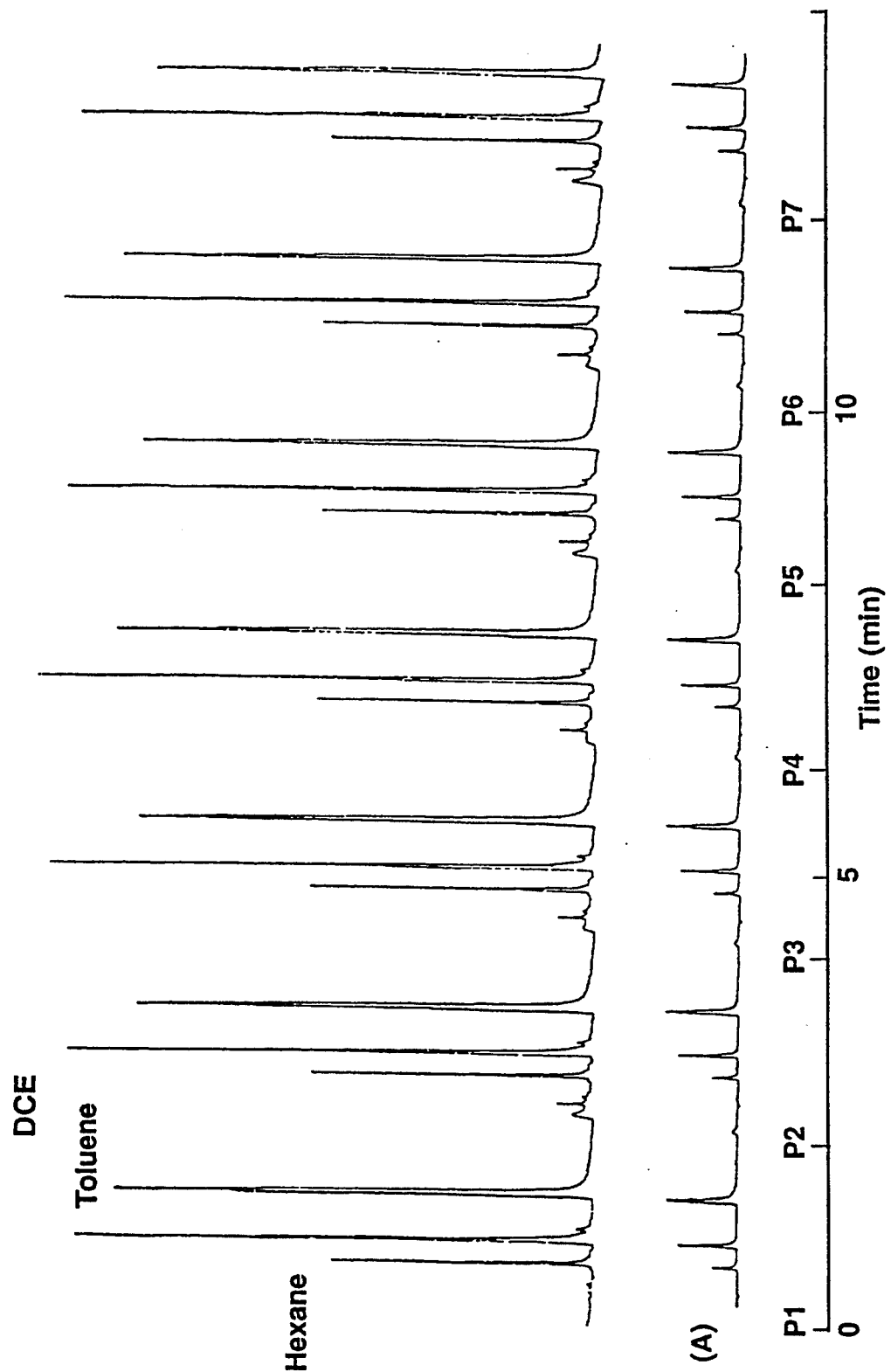
FIG. 3 depicts chromatogram operation of the device shown in FIG. 1 wherein the number of injections are made by the sample valve, followed by an injection pulse by the OLMT with increase in response with the number of valve injections.

By way of further comparison, a small 1 ml injection loop was used to inject gas samples directly from the valve 12 to the GC column 17, with resultant small peaks of minimal sensitivity as shown in FIG. 3A. A series of 10 injections from the small loop was made into OLMT 15, which served to concentrate the samples prior to injection into the GC column 17. The much larger peaks in FIG. 3B were obtained.

Figure 4:
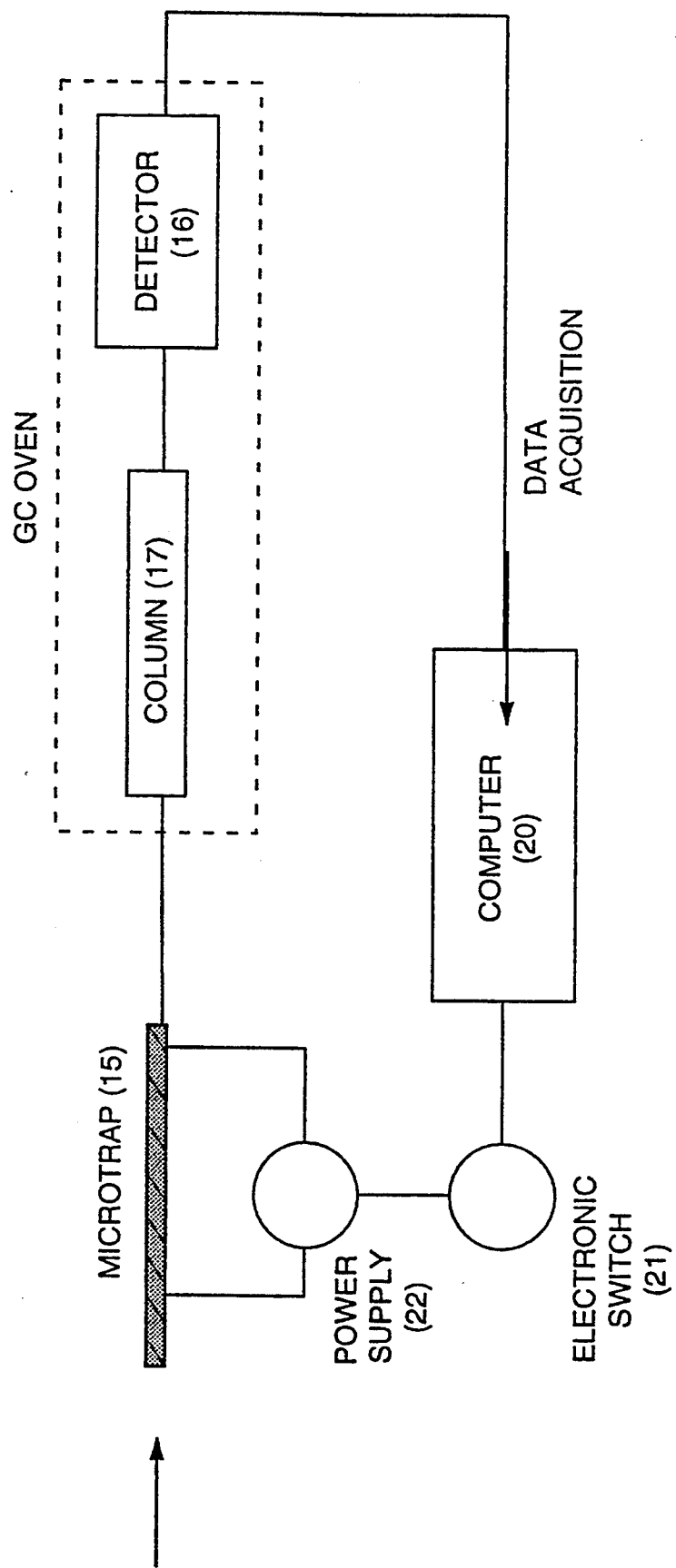
FIG. 4 is a schematic diagram of the continuous monitoring device of the present invention without a sampling valve, i.e., with only OLMT.
Figure 5:
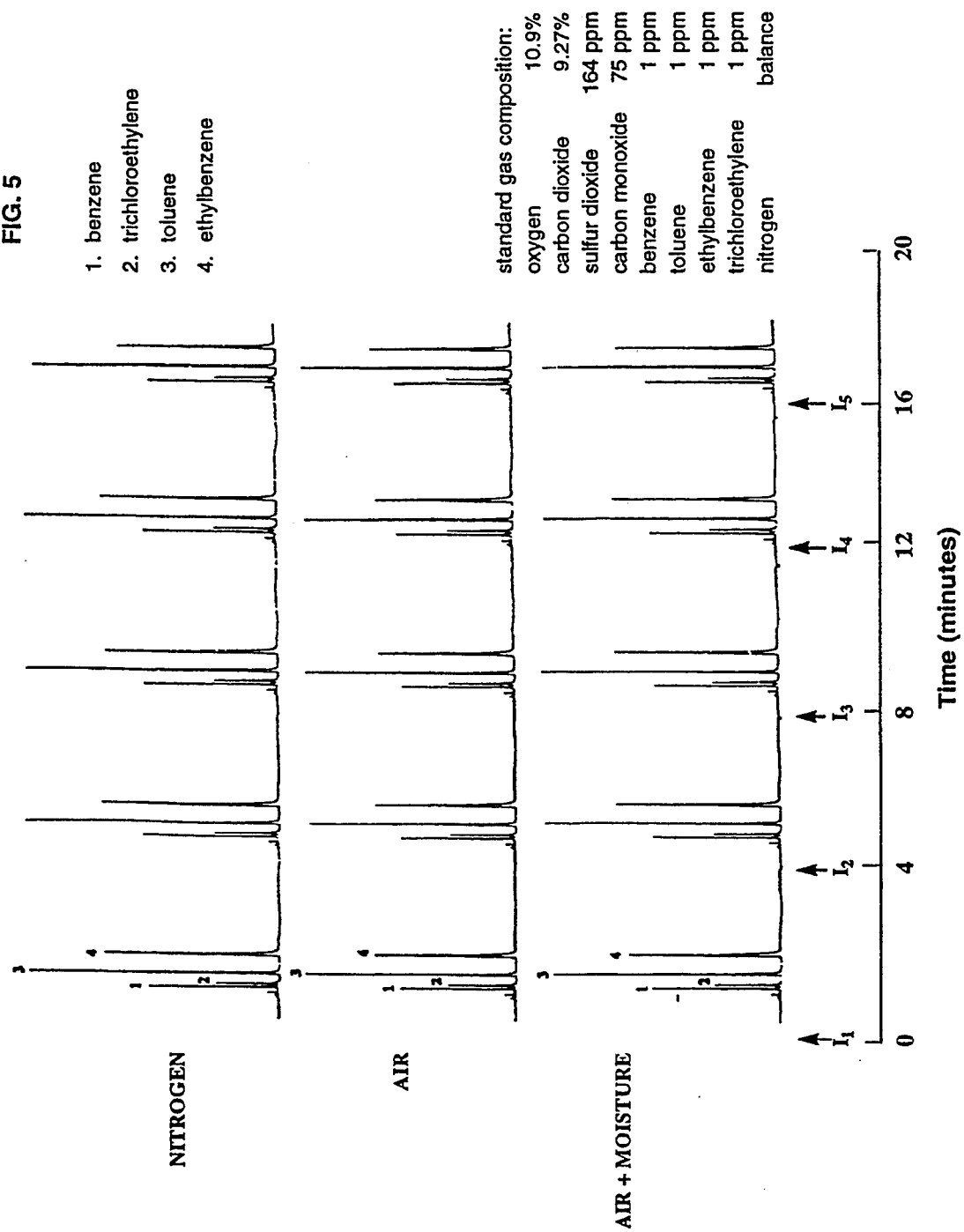
FIG. 5 depicts continuously monitored chromatograms from a simulated stack gas stream using the device of FIG. 4.

The system shown in FIG. 4, with OLMT 15, GC column 17, and detector 16, was utilized in monitoring a simulated stack gas containing the following VOCs at 1 ppm$_v$ each: benzene, toluene, ethyl benzene and dichloroethylene. The standard also contained other combustion products such as $CO_2$, $CO$, $SO_2$, and $O_2$. The standard was diluted 1:1 with $N_2$, air and with air saturated with moisture. The OLMT was operated in the same fashion as mentioned above. A section of the output from recorder 30 is shown in FIG. 5. Excellent results were obtained even in the presence of interfering species in each case. A comparison of OLMT with capillary split/splitless injection was done using benzene, toluene and xylene as the sample. The results are presented in the following table:

| Compounds | Microtrap | | | Injection port | | |
| --- | --- | --- | --- | --- | --- | --- |
| | Benzene | Toluene | p-Xylene | Benzene | Toluene | p-Xylene |
| Retention Time (sec) | 57.38 | 61.85 | 68.41 | 56.27 | 62.22 | 70.97 |
| % RSD of Retention Time | 0.22 | 0.23 | 0.20 | 0.13 | 0.17 | 0.16 |
| % RSD of Peak Height | 1.14 | 0.97 | 1.46 | 1.60 | 1.50 | 2.90 |
| Band Duration *(sec) | 0.76 | 0.78 | 1.12 | 0.80 | 1.00 | 1.20 |
| Terminal Band Length* (mm) | 385.09 | 365.74 | 475.62 | 411.30 | 467.02 | 490.38 |

Reproducibility of retention time as well as peak height was very good for the OLMT, and was comparable to that of the injection port. The trap also produced sharp peaks, as is evident from FIG. 5 and at the same retention time. The terminal band length (measured as the length of the solute band emerging from the end of the column) was somewhat smaller for the trap as compared to the injection port. This was attributed to the fact that flow through the trap is compatible with flow through the column without any dead volume.

Figure 6:
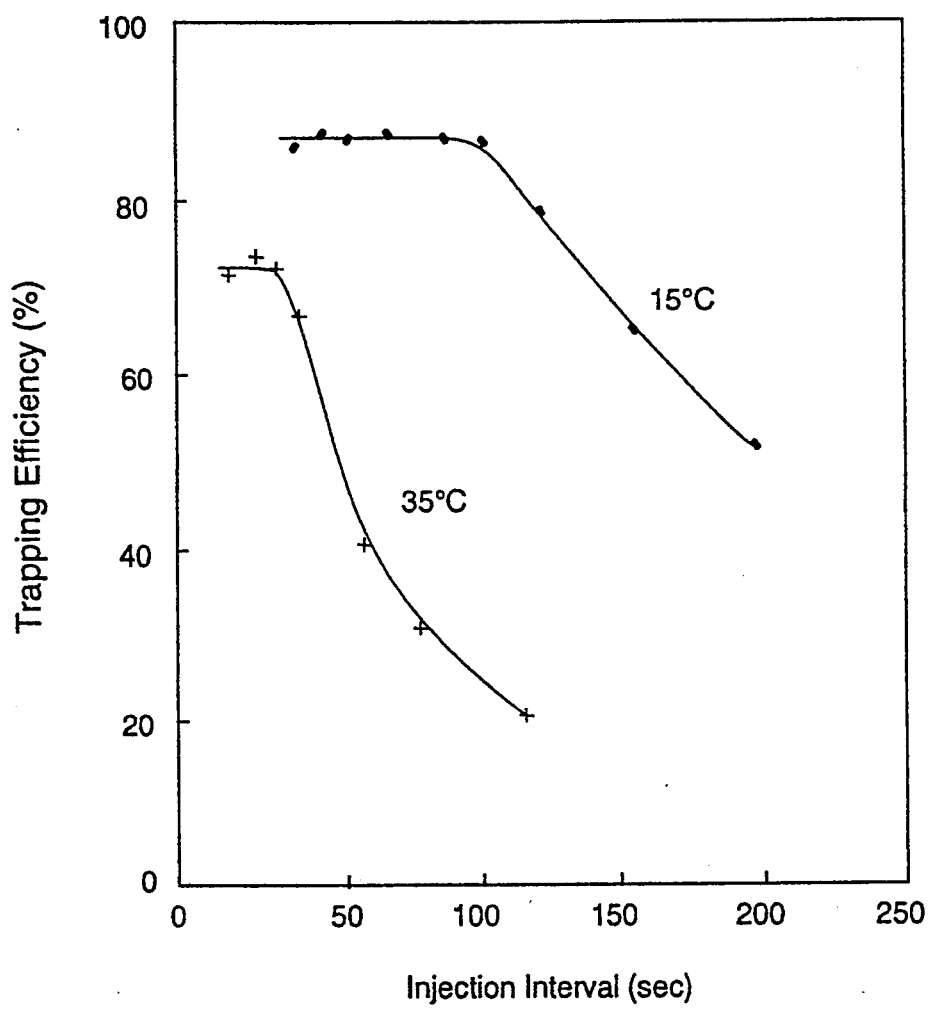
FIG. 6 is a graph depicting trapping efficiency of OLMT as a function of injection interval.

Trapping efficiency as a function of injection interval ($t_i$) is given in FIG. 6 at 15° C. and 35° C., with the lower temperature providing a trapping efficiency of about 90% with a pulse interval of less than 100 seconds. Efficiency drops off sharply thereafter with longer pulse time intervals. At the higher temperature, maximum efficiency is only about 75% up to an injection interval of about 40 seconds.

Figure 7:
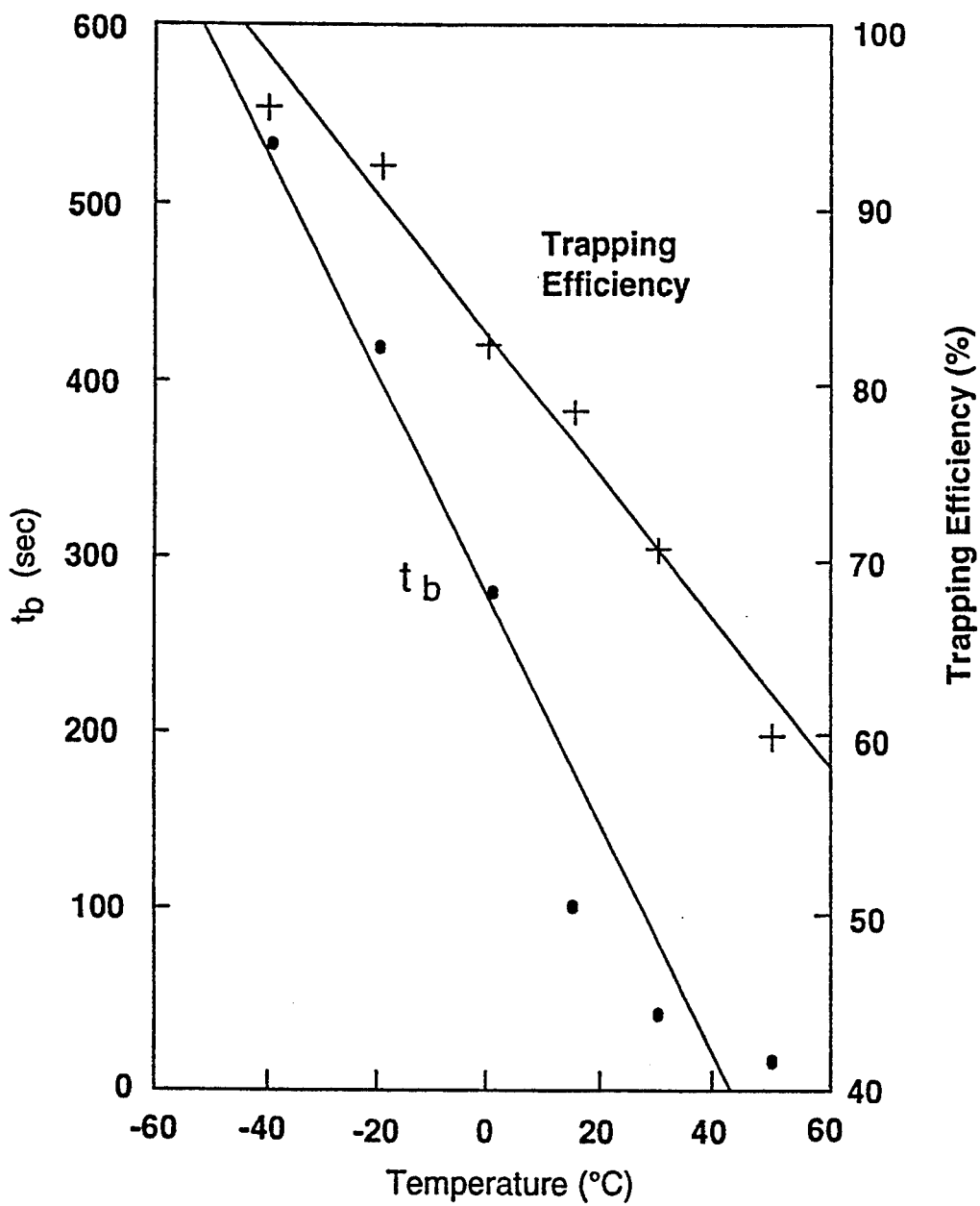
FIG. 7 is a graph showing the dependence of trapping efficiency and breakthrough time of OLMT as a function of OLMT temperature.
Figure 8:
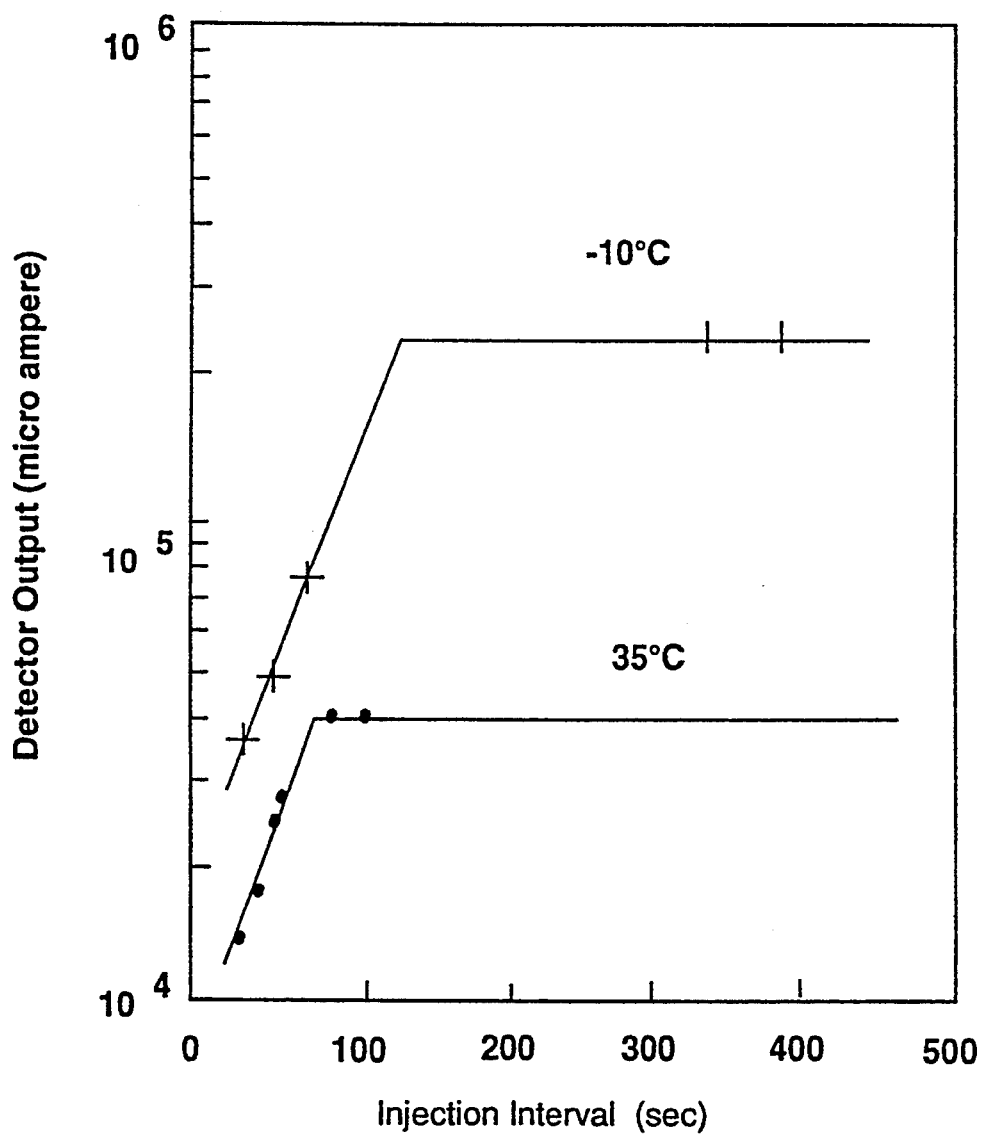
FIG. 8 is a graph of microtrap response as a function of injection interval.

As is evident from the graph of FIG. 7, trapping efficiency is directly proportional to a decrease in temperature and an increase in $t_b$, the time interval for the sample to migrate through the trap. In addition, $t_b$ is directly proportional to temperature change as well. Though lower temperatures are desirable, sub-ambient temperatures are not always required for suitable monitoring. In this regard the output recording of FIG. 2, 3.5 were obtained at room temperature of 22° C. for the three analytes being tested for. The graph in FIG. 8 illustrates the extent of detector output, in microamperes, as a function of injection intervals at the $-10°$ C. and 35° C. temperatures. At an interval of about 110 seconds for the lower temperature and about 80 seconds for the higher temperature, the detector output reaches a maximum. Such output maximum is highly desirable for effective monitoring of the low level concentration VOCs.

Figure 9:
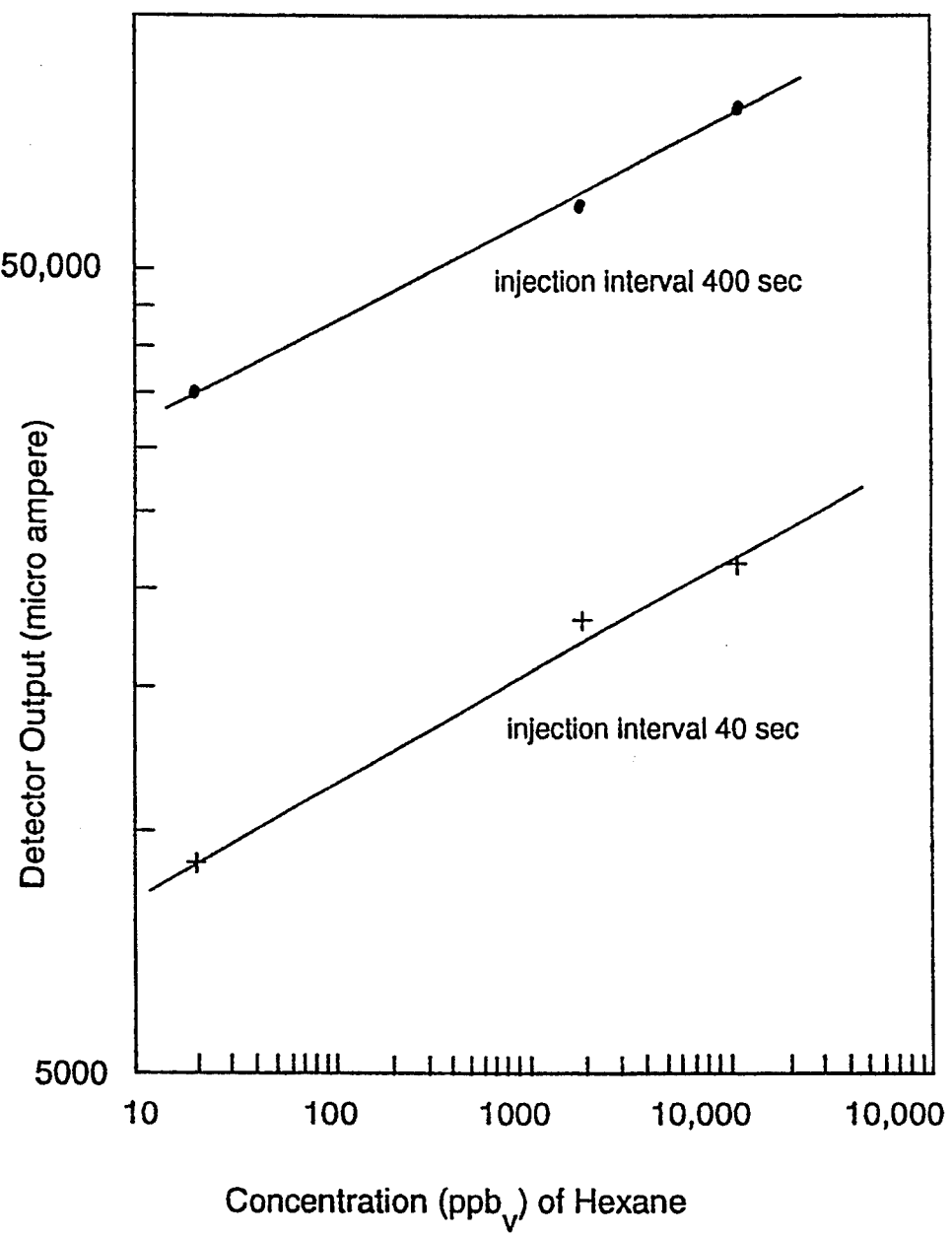
FIG. 9 is a plot of OLMT response as a function of concentration of VOC.

In FIGS. 8 and 9, the specific detector output for the hexane component of the VOCs was plotted against concentration in $ppb_v$ for injection intervals of 400 seconds ($>t_b$) and 40 seconds ($<t_b$). In both instances, linear relationships were obtained. With pulses every 400 seconds, more sample was trapped with resultant greater sensitivity.

The data presented in FIG. 9 indicate that $ppb_v$ levels of VOCs can be effectively monitored by using the OLMT. Thus, for example, for 20 $ppb_v$ hexane, at pulse intervals of 40 seconds, the detector response was 6000 microamps. Since signals of two orders of magnitude lower can be easily measured by the detector, VOCs with sub $ppb_v$ levels can be effectively monitored in accordance with the present invention. For measuring of organics in this detector a response level of approximately 10 microamperes is sufficient. In general, with all detectors, a detector response sufficient to provide a signal to noise ratio of at least 2:1 is sufficient. The micro sorbent trap (of specific efficiency) should, at the ambient operating temperature and pulse intervals, be capable of individual pulses which provide at least such a response.

Figure 10:
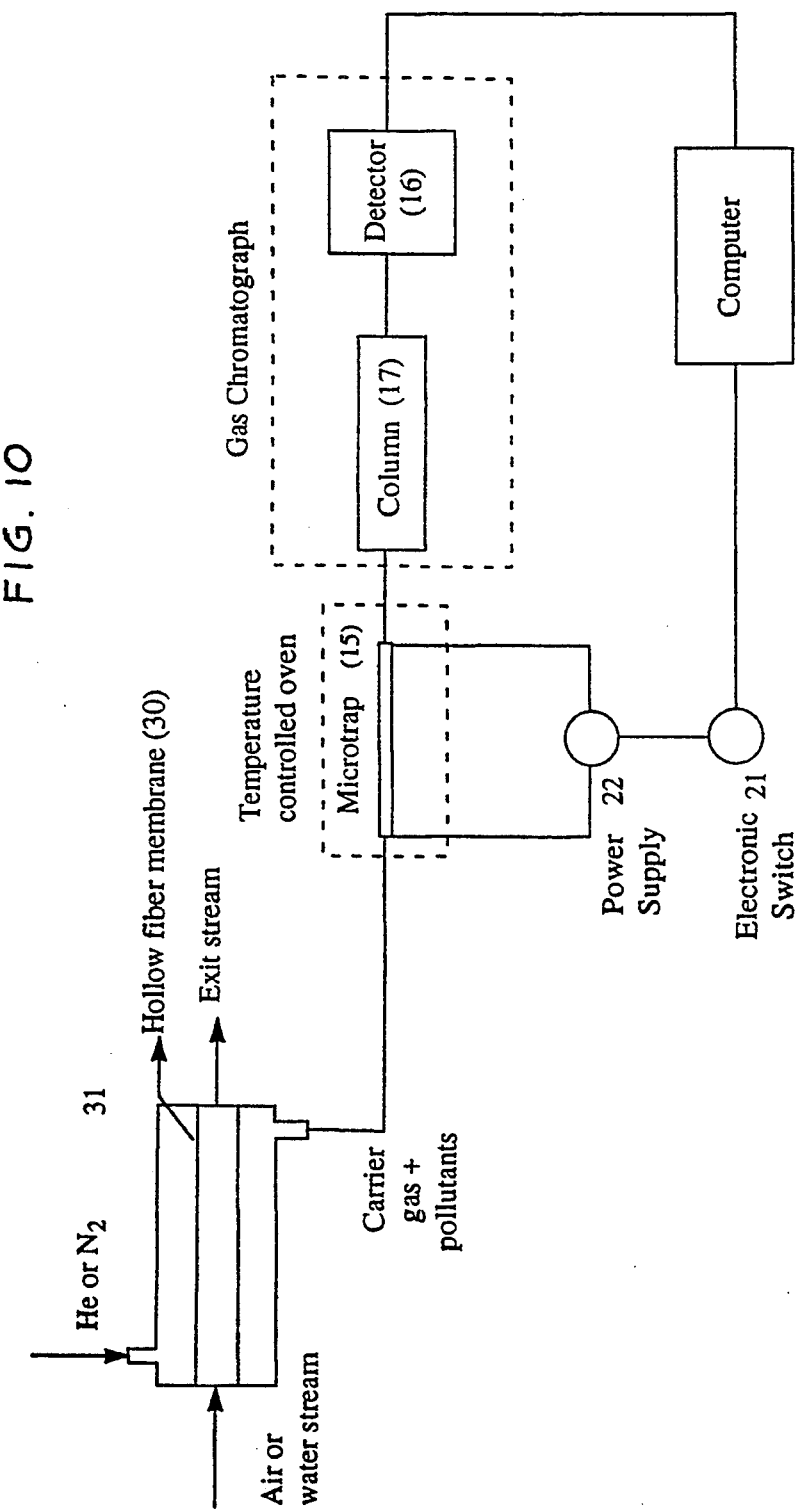
FIG. 10 is a schematic representation of a continuous monitoring process for fluids, using membrane separation.
Figure 11:
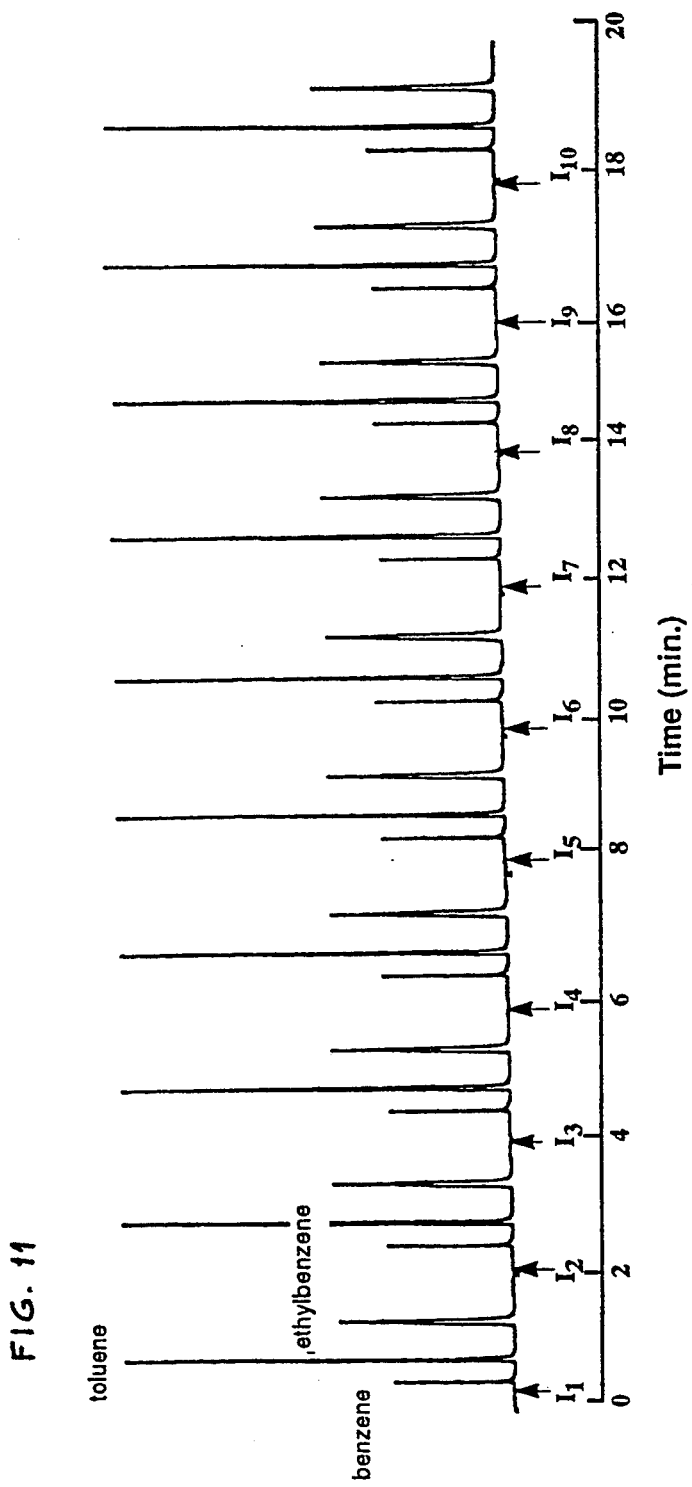
FIG. 11 is a chromatogram example of continuous monitoring of VOCs from a water stream using the technique presented in FIG. 10.

For continuous monitoring of fluids (gases and liquids) water, the system in FIG. 10 was used. Water flowed through the hollow fiber membrane module 31. The VOCs from the water permeated through the hollow fiber 30 and into the carrier gas stream. The carrier gas stream went into the OLMT 15, where the VOCs were trapped. Injections at fixed intervals of time were made by the method described before. The efficiency of the process can be seen from FIG. 11, wherein a water stream containing the VOCs was monitored every two minutes.

It is understood that the above description, Example and drawings are illustrative of the present invention and that changes can be made in the method, testing parameters, instruments and the like without departing from the scope of the present invention as defined in the following claims.

What is claimed is:

1. A device for the monitoring of concentrations, of materials in a fluid stream, said device comprising a sampling valve, a stationary concentrator element and a detector, wherein said valve comprises a sample retention element, with said valve being opened to cause a sample of the stream, with contained materials, to enter and be retained in said sample retention element, said valve being further connected to a source of an inert carrier gas, wherein said sample is entrained on the carrier gas and carried to the concentrator element from the sample retention element, said concentrator element having means for collecting and retaining substantially only said materials, said concentrator element further having injection means to inject at least one sample of the materials into the detector to effect said monitoring.

2. The device of claim 1, wherein the device is adapted for the continuous monitoring of concentrations, as low as sub $ppb_v$, of materials in a fluid stream.

3. The device of claim 1, wherein said concentrator element comprises a micro-sorbent trap capable of releasably continuously adsorbing said samples, but wherein said micro-sorbent trap does not adsorb oxygen or water.

4. The device of claim 3, wherein said concentrator element comprises at least two of said micro-sorbent trap connected in series.

5. The device of claim 3, wherein said concentrator element comprises at least two of said micro-sorbent trap connected in parallel to said sampling valve for separate sample concentrations.

6. A device for the continuous monitoring of concentrations, as low as sub $ppb_v$, of volatile organic compound (VOC) pollutant levels in a fluid stream, said device comprising a sampling valve, a stationary concentrator element and a detector, wherein said valve comprises a sample retention element, with said valve periodically opening to cause a sample of the VOCs to enter and be retained in said sample retention element, said valve being further connected to a source of an inert carrier gas, wherein said sample of VOCs is entrained on the carrier gas and carried to the concentrator element from the sample retention element, said concentrator element having injection means to inject at least one sample of the VOCs into the detector to effect said monitoring.

7. The device of claim 6, wherein the detector comprises a gas chromatograph (GC).

8. The device of claim 7, wherein said concentrator element comprises a micro-sorbent trap capable of releasably continuously adsorbing said samples of the VOCs, but wherein said micro-sorbent trap does not adsorb sufficient oxygen or water.

9. The device of claim 8, wherein the concentration levels of the VOCs in the fluid stream are as low as sub $ppb_v$, with said samples of the VOCs being sufficiently high for accurate monitoring determinations, and wherein the detector provides an electrical response level, and wherein the concentrated, collected samples of the VOCs provide a detector response level with a signal to noise ratio of at least 2.1.

10. The device of claim 8, wherein said injection means comprises means for rapidly heating the micro-sorbent trap with concomitant heating of the collected, concentrated samples of the VOCs.

11. The device of claim 10, wherein said means for rapidly heating the micro-sorbent trap comprises an electric current and wherein said micro-sorbent trap is electrically conductive.

12. The device of claim 11, wherein the micro-sorbent trap comprises a small length of tubing containing an adsorbent.

13. The device of claim 12, wherein the adsorbent is a high surface area adsorbent and is present in an amount sufficient to provide a total surface area, whereby sufficiently large concentrated samples of VOCs can be collected for continuous analysis.

14. The device of claim 13, wherein the diameter of said tubing is at least about 0.5 mm.

15. The device of claim 13, wherein said sample retention element comprises a loop having sufficient volume whereby a single sample of said VOCs provides said sufficient concentration level.

16. The device of claim 13, wherein said sample retention means comprises a loop having a volume whereby a single sample of said VOCs does not provide said sufficient concentration level, with more than one sample of VOCs being required to provide said sufficient concentration level.

17. The device of claim 7, wherein said gas chromatograph is equipped with a column for the measurement of different components.

18. A method for the continuous monitoring of concentrations, as low as sub $ppb_v$, of pollutant levels in a fluid stream, comprising the steps of collecting at least one sample of the pollutants, by collecting means, from the fluid stream; concentrating the at least one collected sample of the pollutants by concentration means; and, at predetermined time periods, desorbing the concentrated, at least one collected sample of the pollutants from the concentration means, by desorption means, and injecting the desorbed, concentrated, at least one collected sample of the pollutants into a detector; wherein the steps are repeated for said continuous monitoring.

19. The method of claim 18 wherein the pollutants comprise volatile organic compounds (VOCs).

20. The method of claim 19, wherein the collecting means and concentration means remain accessible to additional collection of samples of the VOCs during said desorbing.

21. The method of claim 20, wherein at said predetermined time periods, the concentration levels of the concentrated, collected samples of the VOCs are sufficiently high for accurate monitoring determinations.

22. The method of claim 21, wherein the detector comprises a gas chromatograph column (GC).

23. The method of claim 20, wherein said concentration means comprises a micro-sorbent trap capable of releasably adsorbing continuously collected amounts of said samples of the VOCs to said sufficiently high levels, but wherein said micro-sorbent trap does not adsorb oxygen or water.

24. The method of claim 23, wherein the concentration levels of the VOCs in the fluid stream are as low as sub $ppb_v$, with said concentrated, collected samples of the VOCs being sufficiently high for accurate monitoring determinations, and wherein the detector provides an electrical response level, and wherein the concentrated, collected samples of the VOCs provide a detector response level with a signal to noise ratio of at least 2:1.

25. The method of claim 23, wherein components of the samples of VOCs are separated from each other prior to the injection into the GC detector.

26. The method of claim 23, wherein said desorption means comprises means for rapidly heating the micro-sorbent trap with concomitant heating of the collected, concentrated samples of the VOCs.

27. The method of claim 26, wherein said means for rapidly heating the micro-sorbent trap comprises an electric current and wherein said micro-sorbent trap is electrically conductive.

28. The method of claim 27, wherein the micro-sorbent trap comprises a small length of tubing containing an adsorbent.

29. The method of claim 28 wherein the adsorbent is a high surface area adsorbent and is present in an amount sufficient to provide a total surface area, whereby sufficiently large concentrated samples of VOCs can be collected for continuous analysis.

30. The method of claim 29, wherein the diameter of said tubing is at least about 0.5 mm.

31. The method of claim 23, wherein said collecting means comprises a sampling valve having sample retention means, and wherein an inert carrier gas is entrained on a sample of the VOCs for carrying the sample to the micro-sorbent trap.

32. A device for monitoring concentrations of materials in a fluid stream, said device comprising a stationary concentrator element and a detector, said concentrator element having means for collecting and retaining substantially only said materials, and injection means to inject at least one sample of said materials into said detector to effect said monitoring, wherein said concentrator element is in direct fluid connection with said detector.

33. A device for the continuous monitoring of concentrations, as low as sub $ppb_v$, of volatile organic compound (VOC) pollutant levels in a fluid stream, said device comprising a stationary concentrator element, and a detector, said stationary concentrator element adapted to receive a sample of said fluid stream suspected of containing said VOC, said sample having been entrained in a carrier gas and being delivered to said concentrator element, said concentrator element residing in direct fluid connection with said detector and having injection means to inject at least one said sample into said detector to effect said monitoring.

34. The device of any of claims 1, 6, 32 or 33, wherein said collecting means comprises a fiber membrane which separates the VOCs from the fluid stream, wherein, after separation of a sample of VOCs from the fluid stream, an inert carrier gas is entrained on the sample of the VOCs for carrying the sample to the micro-sorbent trap.

35. The method of claim 34, wherein said fluid stream is a liquid.

36. The device of any of claims 1, 6, 32 or 33, wherein said sample retention means comprises a loop having sufficient volume whereby a single sample of said VOCs provides said sufficient concentration level.

37. The device of any of claims 1, 6, 32 or 33, wherein said sample retention means comprises a loop having a volume whereby a single sample of said VOCs does not provide said sufficient concentration level, with more than one sample of VOCs being required to provide said sufficient concentration level.

* * * * *